United States Patent [19]
Gagnon et al.

[11] Patent Number: 5,470,757
[45] Date of Patent: Nov. 28, 1995

[54] SPECTROSCOPIC SAMPLE HOLDER AND METHOD FOR USING SAME

[75] Inventors: James E. Gagnon, Minneapolis; Neale P. Povey, Stillwater; David R. Gagnon, St. Paul; Roland R. Midgley, Minneapolis, all of Minn.

[73] Assignee: Minnesota Mining and Manufacturing Company, St. Paul, Minn.

[21] Appl. No.: 267,839

[22] Filed: Jun. 28, 1994

Related U.S. Application Data

[63] Continuation of Ser. No. 903,578, Jun. 24, 1992, abandoned, which is a continuation-in-part of Ser. No. 720,713, Jun. 25, 1991, abandoned.

[51] Int. Cl.[6] ............................ G01N 21/00; G01N 1/00; G01N 21/01
[52] U.S. Cl. ........................ 436/164; 436/169; 436/170; 422/58; 422/82.08; 422/82.09; 356/36; 356/244
[58] Field of Search .................................... 422/58, 82.08, 422/82.09; 436/164, 169, 170; 356/36, 38, 244

[56] References Cited

U.S. PATENT DOCUMENTS

| | | | |
|---|---|---|---|
| 3,341,960 | 9/1967 | Florjancic et al. | 40/152 |
| 3,736,421 | 5/1973 | Strange et al. | 250/341 |
| 3,953,566 | 4/1976 | Gore | 264/505 |
| 3,962,153 | 6/1976 | Gore | 521/79 |
| 4,042,335 | 8/1977 | Clement | 435/805 X |
| 4,096,227 | 6/1978 | Gore | 264/110 |
| 4,110,392 | 8/1978 | Yamazaki | 264/127 |
| 4,187,390 | 2/1980 | Gore | 174/102 R |
| 4,194,041 | 3/1980 | Gore et al. | 428/252 |
| 4,387,990 | 6/1983 | Yazawa et al. | 422/58 X |
| 4,405,560 | 9/1983 | Murata | 422/102 |
| 4,539,256 | 9/1985 | Shipman | 428/315.5 |
| 4,570,494 | 2/1986 | Dunn et al. | 73/863.22 |
| 4,637,978 | 1/1987 | Dappen | 435/805 X |
| 4,668,472 | 5/1987 | Sakamoto et al. | 422/58 |
| 4,668,619 | 5/1987 | Greenquist et al. | 435/805 X |
| 4,849,457 | 7/1989 | Ichii et al. | 521/62 |
| 4,871,824 | 10/1989 | Heilmann et al. | 435/180 X |
| 4,931,384 | 6/1990 | Layton et al. | 436/164 X |
| 4,942,297 | 7/1990 | Johnson et al. | 250/304 |
| 4,992,382 | 2/1991 | Porter et al. | 422/55 X |
| 5,049,487 | 9/1991 | Phillips et al. | 422/58 X |
| 5,082,516 | 1/1992 | Akao et al. | 422/58 X |
| 5,096,668 | 5/1992 | Thompson et al. | 435/805 X |
| 5,118,608 | 6/1992 | Layton et al. | 435/805 |
| 5,334,837 | 8/1994 | Ikeda et al. | 250/339 |

FOREIGN PATENT DOCUMENTS

WO83/00391 2/1983 WIPO.
WO90/15981 12/1990 WIPO.

OTHER PUBLICATIONS

Owen, et al., *J. Chem. Ed.*, 64 (11), 1987, pp. 976–979.
Love and Wool, *A.C.S. Polymeric Material Science and Engineering*, vol. 53, 1985, pp. 317–320.
Afran and Newberry, *Spectroscopy*, 6(1), 1990, pp. 31–33.
Andrade, *J. Chem. Ed.*, 66(10), 1989, p. 865.
Baker et al., *Membrane Separation Systems—A Research and Development Needs Assessment*, Final Report, vol. 2, U.S. Dept. of Energy, Office of Program Analysis, Apr. 1990.
Benson, *European Plastic News*, 1989, p. 26.

(List continued on next page.)

Primary Examiner—Robert J. Warden
Assistant Examiner—Christopher Y. Kim
Attorney, Agent, or Firm—Gary L. Griswold; Walter N. Kirn; Robert H. Jordan

[57] ABSTRACT

A sample holder for use in infrared spectrophotometric analysis. The holder comprises a microporous sheet and is particularly useful for analysis of solutions, colloids, small particle solids, flowable solids, solvents, and viscous fluids. The microporous sheet preferably has a low absorbance (high spectral transmittance) in infrared wavelengths. The sample holder is especially useful for the analysis of aqueous based samples. Also, a method for using such sample holders for infrared spectrophotometric analysis.

18 Claims, 1 Drawing Sheet

OTHER PUBLICATIONS

Chalzel, "A Spectrophotometer Cell for UV Spectral Measurements of Liquids at High Temperatures and Pressures," *J. of Physics E: Scientific Instruments*, vol. 10, 1977, pp. 633–634.

Dove and Hallett, *Chemistry and Industry*, 1966, pp. 2051–2053.

Jackson, "Novel Sampling and Support Media for the Infrared Analysis of Water–immiscible Oil–based Environmental Pollutants," *Analyst*, Mar., 1984, vol. 109, pp. 401–402.

Osland, *Laboratory Practice*, 37(2), 1988, p. 73.

Pasto and Johnson, *Organic Structure Determination*, Prentice–Hall, Inc., 1969, pp. 145–147.

Prasad, et al., "Nondispersive Solvent Extraction Using Microporous Membranes" AIChE Symposium Series, No. 261, vol. 84, 1988, pp. 42–53.

ASTM F 316–86—Standard Test Methods for Pore Size Characteristics of Membrane Filters by Bubble Point and Mean Flow Pore Test, 1986.

ASTM D 726–84—Standard Test Method for Resistance of Nonporous Paper to Passage of Air, 1984.

ASTM D 792–86—Standard Test Methods for Specific Gravity (Relative Density) and Density of Plastics by Displacement, 1986.

ASTM D 4197–82—Standard Test Methods for Percent Porosity of Membrane Filters, 1983.

Ratajczykowa et al., "A metal UHV infrared cell for characterisation of supported metal catalysts," *Journal of Physics E: Scientific Instruments*, vol. 21, No. 9, Sep. 1988, Bristol, GB, pp. 906–907.

SPECTROSCOPIC SAMPLE HOLDER AND METHOD FOR USING SAME

CROSS-REFERENCE TO RELATED APPLICATION

This is a continuation of U.S. application Ser. No. 07/903,578, filed Jun. 24, 1992, now abandoned which is a continuation-in-part of U.S. application Ser. No. 07/720,713, filed Jun. 25, 1991, now abandoned.

FIELD OF THE INVENTION

The present invention relates to sample holders for use in infrared spectroscopic analysis and their use.

BACKGROUND OF THE INVENTION

In infrared ("IR") spectroscopy a beam of light from an infrared source is passed through a sample. The light that is transmitted through the sample is evaluated in comparison with the incident light and its intensity plotted as a function of wavelength or wavenumber. Wavenumber is expressed herein as centimeters$^{-1}$ or "cm$^{-1}$". This spectral plot or spectrum can provide information regarding the functional groups and structural features of the sample and, accordingly, IR spectroscopy has become a valuable tool in analytical chemistry for certain types of samples.

The infrared region of the electromagnetic spectrum extends from the upper end of the visible region (wavenumber of approximately 14,300 cm$^{-1}$) to the microwave region (near 20 cm$^{-1}$). The region which is typically of most interest to analytical chemists for determination of structural features of an organic sample is from about 4000 cm$^{-1}$ to about 400 cm$^{-1}$. In this region of the spectrum, organic compounds absorb incident infrared light at frequencies corresponding to the vibrational frequencies of the compound. These absorbed frequencies are characteristic of the structural features of the compound or compounds in the sample and can permit rapid identification. The intensities of the peaks in the spectral plot or spectrum are a function of the concentration of the sample, extinction coefficient, and path length of the incident light through the sample.

To obtain an infrared spectrum of a sample, the sample is typically applied to a sample holder or "cell". This sample holder or cell holds the sample in the path of the incident beam of infrared light. It is essential that the material used for the sample holder be highly transmissive in that region of the IR spectrum which is of interest. Also, the sample holder should not be soluble in, or reactive with, either the sample or solvent (if any). Illustrative examples of materials used in sample holders include inorganic salts, glasses, and quartz.

Sodium chloride (NaCl) is perhaps the most commonly used material since it does not absorb infrared light in the range of 4000 to 625 cm$^{-1}$ and is relatively less expensive than some alternatives. However, NaCl crystals are very susceptible to moisture and easily broken. For a discussion of cell materials see Pasto and Johnson, *Organic Structure Determination*, Prentice-Hall, Inc., 1969, pp. 145–147.

In the majority of analyses, the holder (or cell) is a pair of plates made from crystals of an inorganic salt that has been precisely machined and polished for maximum optical clarity. A sample is then placed between the pair of plates and mounted by a variety of techniques in the beam of infrared light. Solid samples are often ground and intimately mixed with an inorganic salt such as potassium bromide, pressed into a thin wafer or pellet, applied to a sample holder, and mounted in the infrared beam. Alternatively, samples may be mulled with an oil such as NUJOL™ mineral oil, applied to a sample holder, and analyzed as a thin film. Liquid samples, either neat or in solvent, may also be analyzed using a sealed cell in which a pair of plates are sealed together with a spacer to provide a chamber in which the sample is held. In addition to the use of plates, other sample preparation techniques have been developed. For instance, liquids or solutions having a relatively high surface tension such as aqueous solutions have been analyzed by suspending a thin film from a loop of wire. Also, a solution may be coated and dried to form a film, e.g., a solution may be coated on a film of polytetrafluoroethylene and dried, and the resulting thin film peeled from the polytetrafluoroethylene and analyzed.

Due to the susceptibility of many known cell materials to degradation by moisture and the long drying time necessary for preparation of some samples, analysis of aqueous samples is difficult. Increasingly stringent regulations have prompted many industries to reduce or eliminate organic solvent use and emissions, prompting the development of water-based processes and products. Illustrative examples of materials that have been used for cells for use with aqueous samples include silver bromide, calcium fluoride, and barium fluoride. Use of such materials is limited by the typically high expense, limited useful spectral ranges, burdensome maintenance, and difficult sample preparation associated with such materials. Typically, aqueous samples are analyzed using a horizontal attenuated total reflectance ("ATR") crystal to which a sample is applied. A beam of infrared light is reflected repeatedly through the sample before being evaluated in a detector. Use of this technique is hampered by the high cost of sample holders and difficulties encountered in sample preparation and maintenance. In part due to these problems, IR spectroscopy has not reached its potential as a routine tool for analysis of aqueous samples.

In addition to the problems described, namely cost, sensitivity to moisture and fragility, commercially available cells have high maintenance requirements. In view of the high costs, disposal of these cells is prohibitive. Accordingly, sample holders must be carefully cleaned, typically with organic solvents, after each analysis to prevent contamination from one sample to the next. In some instances, the solvents may present health risks to operators. In addition, the high cost of sample holders tends to inhibit retention of samples on a long term basis.

Dove and Hallett, Chemistry and Industry, 1966, pp. 2051–53, describe an all-plastic evacuable cell to be used for infrared or ultraviolet spectroscopic analysis of gases. The cell has windows that can be made from RIGIDEX™ Type 35 polyethylene. The relative thickness of the windows, i.e., about 3 millimeters, would preclude the use of such sample holders in most routine IR spectroscopic analysis due to the strong absorbances. Andrede, *J.Chem. Ed.*, 66(10), p. 865, 1989, describes using polyethylene film as windows in a sample cell. For sampling of liquids the author suggests applying the sample to a film stretched over a ring, covering the sample with a second film, and securing both stretched films with a second ring.

IR spectroscopy has been used as a tool in the analysis of polymer films. Osland, *Laboratory Practice*, 37(2), p. 73, 1988, describes a heated press used to prepare plastic films for analysis by IR. Love and Wool, *A.C.S. Polymeric Material Science and Engineering*, analyzes semi-crystalline polymer films by Fourier Transform Infrared Spectroscopy (FTIR). Benson, *European Plastics News*, p. 26, 1989, describes using IR radiation to measure the thickness or gauge of polymer films.

Owen and Wood, *J.Chem. Ed.*, 64(11), 1987, pp. 976–79, describe the use of tissue paper as a support matrix to obtain infrared spectra of solids and non-volatile liquids. This method would appear to be impractical due to the fragility of the paper and the strong interfering absorbances of the cellulose. As a result, the signal-to-noise ratio or sensitivity is quite low.

Jackson, "Novel Sampling and Support Media for the Infrared Analysis of Water-immiscible Oil-based Environmental Pollutants", *Analyst*, vol. 109, March 1984, pp. 401–02, discloses the use of stretched polytetrafluoroethylene tapes as a support medium for recovery and infrared spectroscopic analysis of water-immiscible organic pollutants.

U.S. Pat. No. 4,942,297 (Johnson et al.) discloses an apparatus for collection and infrared spectroscopic analysis of aerosol-borne particulates.

Thus, there is a need for a commercially available sample cell that is inexpensive, easy to use, insensitive to or non-reactive with liquids such as water or organic solvents, and has a useful spectral range for most routine analysis.

SUMMARY OF THE INVENTION

The present invention provides a novel sample holder for use in manual and automated transmission infrared ("IR") spectroscopic analysis and a novel method for using such sample holders. Sample holders of the invention are simple to use, permit simplified sample preparation, and provide precise and accurate spectra of samples. The sample holders provided herein can be sufficiently inexpensive to permit being discarded or stored after a single use. They also eliminate the need for sample clean up and post-analysis reconditioning of the sample holder. The elimination of such clean up and reconditioning provides improved safety, particularly in cases of hazardous samples and cleaning agents, as well as greater convenience and time economy. In some embodiments, sample holders of the invention may be used with aqueous samples. The sample holders provided herein can provide exceptional spectral accuracy, with embodiments that are essentially inert with the sample and that exhibit minimal substrate absorbances or artifacts so as to not interfere with the spectra obtained.

In brief summary, a sample holder of the invention comprises a microporous sheet having two major surfaces or faces and a support member which facilitates mounting the holder in a spectrometer. In some embodiments, the holder further comprises an aperture shield.

BRIEF DESCRIPTION OF DRAWING

The invention will be further explained with reference to the drawing, wherein.

These figures, which are idealized, are not to scale and are intended to be merely illustrative and non-limiting.

DETAILED DESCRIPTION OF ILLUSTRATIVE EMBODIMENTS

Figure 1:
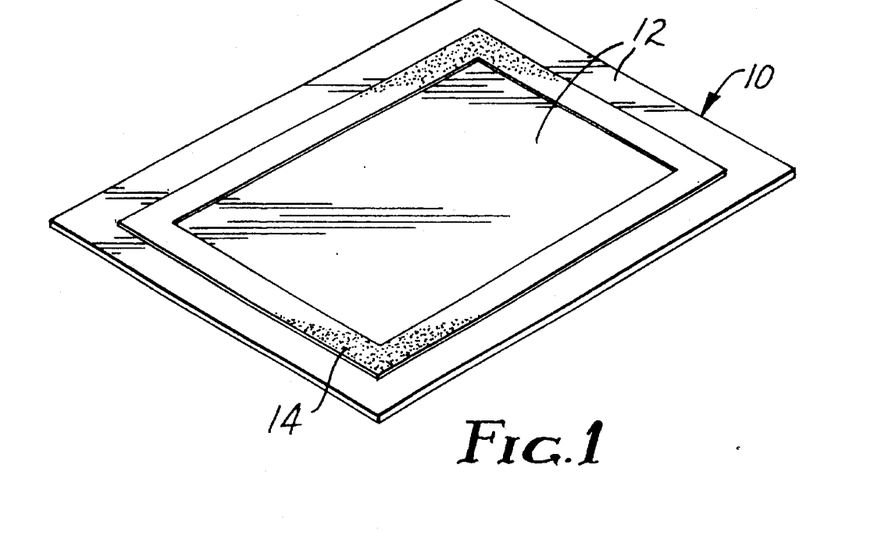
FIG. 1 is a plan view of one face of an illustrative embodiment of a sample holder of the invention.

FIG. 1 illustrates sample holder 10 comprising microporous sheet 12 and support member 14. Sheet 12 is preferably inert, i.e., non-reactive, with the samples to be applied thereto, including any solvents they may contain.

Sheet 12 is preferably very thin, typically being less than about 150 microns, preferably between about 2.5 and about 25 microns, thick. Thicker films tend to lead to greater interference due to the stronger spectral absorbances of the films. Polymeric sheets used in the invention may typically have a basis weight between about 0.03 and 1.0 grams/square meter. Sheets with lower basis weights may be used in some instances, but may tend to be too weak to support sample material. Sheets with higher basis weights may be used in some instances, but may tend to interfere undesirably with spectroscopic analysis.

The observed transmittance of the sheet is a function of sheet thickness, porosity, infrared light scattering characteristics, and composition. It may also depend in part upon the particular wavelength or wavenumber region of interest. The standard deviation (n=20) of the sheet transmittance variability, i.e., the variation in transmittance of the sheet at different locations, is preferably less than about 25 percent relative, more preferably less than about 10 percent relative. In order to ensure highly probative evaluation of sheet transmittance variability, it is typically measured at a wavenumber at which the sheet has an absorbance of about 0.7 to about 1.0 absorbance units, e.g., at the 1460 $cm^{-1}$ absorbance for polyethylene sheets. When using a dual beam (dispersive) instrument a small standard deviation in sheet variability facilitates more accurate subtraction of the absorbances of the sample holder from those of the sample on the holder. Similarly with FTIR instruments a small standard deviation in variability permits subtraction of one standard reference spectrum from those of later analyses.

The sheet may be of any size (area) sufficient to accommodate a sample applied thereto and permit mounting in the desired instrument with a suitable support member. For reasons of instrument size limitations, the size (area) of the sheet to which a sample may be applied is typically preferably small, ranging from less than 1.0 $centimeter^2$ to about 6 $centimeter^2$ per each face in many instances. It will be understood that larger or smaller sheets may be used in accordance with the invention. The increase in sensitivity of modern instruments enables the taking of spectra of very small samples, therefore small sizes of microporous sheets may be used.

The void volume of sheet 12 is typically greater than about 20 percent and preferably greater than about 50 percent. Many useful microporous polymer films are open structures wherein only a fraction of the total volume is occupied by the polymer material. With sample holders made with such films, a greater portion of the matter in the beam path is the sample itself. Conventional non-microporous films are typically less useful and in many instances inoperable for use herein. In many instances, samples applied to conventional films fail to effectively wet the surface of the film. As a result, the sample beads up on the film and tends to run off the film when mounted in the spectrophotometer. Surprisingly, we have found that when applied to microporous sheets made from the same polymers, the same samples will tend to wet out the sheet, enabling the sample to be spectroscopically analyzed. If the sample is analyzed quickly after application to the sample holder, such as by FTIR, the solvent portion of the sample may be spectroscopically analyzed. Alternatively, the sample may be retained for a time to permit the solvent portion to evaporate, leaving the non-volatile portion deposited on the sample holder for subsequent analysis.

It has also been found that, by using microporous sheets as provided herein, acceptable spectra may be taken of samples that readily crystallize when put on a flat surface for a time. Prior to this invention it had been considered difficult to obtain spectra of crystalline samples due to the dispersive and reflective effects of the crystal lattice. It is believed that use of a microporous sheet in accordance with the invention either retards crystallization, or limits crystal growth due to constrainment of the pore size, reducing the previously encountered dispersive and reflective effects of the crystal lattice so as to permit effective spectroscopic analysis.

Although it is believed that any microporous polymeric film may be used as a sheet in the sample holder to provide some of the advantages of the invention, the sheet should be selected to reduce spectral interference of the inherent absorbances of the polymer with the bands being analyzed in the sample. Although each film has characteristic absorbances, the absorbances may be in regions of the infrared spectrum that do not interfere with the absorbances of the sample. In other words, the microporous sheet preferably exhibits relatively low absorbance, i.e., is highly transmissive, in the spectral region(s) of interest. For instance, as discussed below, except for the region of about 3000 to about 2800 $cm^{-1}$ where its aliphatic carbon-hydrogen stretching is evident as strong absorbances, sheets of polyethylene may be used in sample holders of the invention to perform infrared spectroscopic analysis across the range of about 4000 to about 20 $cm^{-1}$. Polyethylene exhibits a limited number of other signals in other portions of the range, but these are typically narrow, well-defined absorbances that are easily taken into account. TEFLON™ films and KEL-F™ films (chlorotrifluoroethylene polymers and copolymers) are typically useful in the range of about 4000 to about 1500 $cm^{-1}$.

The importance of this criterium may be ameliorated by use of modern spectroscopic instruments that have the capacity to "subtract" background absorbances due to solvents, the cell, the atmosphere, etc. In a dispersive type instrument, the infrared beam is split into two parallel beams, one through the sample, and the second, or reference beam, through a "blank" cell. When taking a spectrum of a sample dissolved in solvent, a cell containing only pure solvent is placed in the reference beam so that the instrument can subtract the spectrum of the solvent from that of the dissolved sample. More recent advances in electronics have allowed the spectrum of the background of a blank or reference cell to be scanned and electronically stored so that it may be subtracted from sample spectra collected later.

The process of subtraction of background absorbances which may be imperfect with conventional sample holders may also be imperfect with sample holders of the invention because absorbances may not be cleanly subtracted and may interfere with the absorbances of the sample, particularly when the sample exhibits subtle absorbances which can be inadvertently masked or lost by the subtraction process. Accordingly, the microporous sheet used in the present invention is preferably selected to minimize, and more preferably eliminate, interference of the absorbances of the microporous sheet with the sample, if possible. As the IR spectra of many polymer films are well known, it is simple to choose an appropriate sheet for use in accordance with the present invention.

Selection of a sheet for making a sample holder for a particular application will be dependent in part upon the composition of the sample and analysis to be performed thereon. Microporous sheets may be evaluated for use in particular applications in accordance with the invention by measuring the baseline transmittance or absorbance of the sheet. The transmittance ("T") is the ratio of the power of the infrared radiation that is received by the detector after passing through the sheet to the power of the infrared radiation which is incident to the sheet and is expressed in percent. Absorbance ("A") is the negative of the log of transmittance, i.e., $A = -\log T$. Polymeric films typically scatter a portion of the light incident thereto. In holders of the present invention, the average baseline of the microporous sheet in the range of about 4000 to about 400 $cm^{-1}$ is greater than about 1, preferably greater than about 10, and more preferably greater than about 50, percent transmittance. Expressed in terms of absorbance units, the sheet has an absorbance of less than about 2, preferably less than about 1, and more preferably less than about 0.3. The average baseline absorbance of a sheet is readily determined by obtaining the absorbance of the background, i.e., empty sample holder with no sheet, and the absorbance of subject sheet at about 4000 and about 400 $cm^{-1}$. The aperture opening for both the background and sheet absorbances should have equivalent dimensions. The background absorbances are then subtracted from the sheet absorbances at about 4000 and about 400 $cm^{-1}$, respectively, the resultant values are then added together and divided by 2 to obtain the average baseline absorbance.

A preferred film for sheet 12 for many applications is microporous polyethylene. Polyethylene exhibits a relatively simple spectrum consisting of only four distinctive absorbances in the region of about 4000 $cm^{-1}$ to about 400 $cm^{-1}$ at 2918, 2849, 1465, and 721 $cm^{-1}$, the latter two being of relatively low intensity, allowing its spectrum to easily be subtracted from the sample spectra. Polyethylene having a degree of substantial crystallinity has two additional absorbances caused by the splitting of the latter two absorbances into pairs of peaks. In addition, polyethylene is inert to many chemicals, is insensitive to moisture, and provides strong, e.g., tear and puncture resistant films at low thicknesses. An illustrative example of another polymer that may be useful in sample holders of the invention, particularly where the carbon-hydrogen bond (C—H) stretching region is of significant interest, is microporous polytetrafluoroethylene (PTFE). PTFE has no absorbances above about 1500 $cm^{-1}$ so the C—H stretching region which is at about 3000 to about 2800 $cm^{-1}$ is not subject to interfering absorbances.

Microporous polymer sheets may be characterized as having a plurality of interconnecting microscopic pores opening through at least one face of the sheet. The pores may open through only one or both faces of the sheet. In the event they open through only one surface, the sample is typically placed on that face. Preferably the pore size distribution across the portion of the sheet to which a sample may be applied is substantially uniform so as to provide a low sheet transmittance variability as discussed above. The pore sizes typically range from about 0.1 to about 50 micrometers in their "average characteristic width". As used herein, "average characteristic width" means the average of the largest of the cross-sectional dimensions of the pores, e.g., pore diameter if they are substantially circular in cross-section. The pore density is such that the void volume of the sheet in that portion, as measured by ASTM D4197-82, is typically greater than about 20 percent, preferably in the range of about 50 percent to about 98 percent, and more preferably between about 70 percent and about 85 percent. In general, the greater the void volume, the more readily the solvent evaporates from a sample loaded onto the sheet. In addition, with greater void volume the inherent absorbances of the sheet are less likely to interfere with analysis of the response of the sample. At very high void volumes, however, the sheet may not possess sufficient structural integrity to permit convenient handling of the sample holder and sample during preparation, analysis, storage, etc. The pore configuration is not believed to be critical. For instance, sheets with uniform, substantially circular pores formed by laser ablation or nuclear etching, sheets made of fibrillated masses with openings of varying size and configuration, sheets made of non-woven materials, and sheets made of strands having uniform diameter of material defining a tortuous path (e.g., random or fixed) through the sheet may be used in sample holders of the invention. As used herein, "microporous" describes sheets having any such openings.

As used herein, "microporous sheets" also includes polymeric sheets having at least one structured surface wherein the surface has surface voids, grooves, depressions, etc. having a minimum depth of about 0.1 micron and a minimum width of about 0.1 micron therein, typically having an average characteristic dimension of at least between about 0.1 and about 50 microns, sometimes even substantially larger. As used herein, "average characteristic dimension" means the average of the largest dimension of the structure element in a plane parallel to the transit opening of the sample holder. Such sheets may be formed from solid polymeric sheets by a variety of surface modifying and replication techniques, including but not limited to laser ablation, molding, embossing, extrusion, etc. Such surface features can increase the sample holder's retention of sample material, especially particulate materials. Structured surface features may also be formed on microporous sheets having a plurality of pores as described above.

Composite sheets comprising a base sheet, e.g. a microporous sheet as described above, bonded to an open mesh may be used. The mesh facilitates collection and retention of sample material. The base sheet supports the sample material in the transit opening. The composite sheet must meet the transmittance criteria described herein, but because the mesh is open, the mesh's bulk properties need not meet those transmittance criteria.

U.S. Pat. No. 4,539,256 (Shipman) discloses microporous sheet materials and methods for making same. Many of these materials may be used in sample holders of the invention. Various patents to W. L. Gore and Associates, Inc., including U.S. Pat. Nos. 3,953,566, 3,962,153, 4,096, 227, 4,110,392, 4,187,390 and 4,194,041 describe the preparation of porous articles, including microporous sheets, from polytetrafluoroethylene,, Many of the polymeric materials described in those patents may be used in accordance with the present invention.

Many types of microporous polymer sheets useful in some embodiments of the invention, in a variety of polymers, thicknesses, and void volumes are commercially available. Among these are ADVENT™ film, a microporous polyethylene film, available from 3M, CELGARD™ films, hydrophobic or hydrophilic microporous polyethylene or polypropylene films available from Hoechst Celanese, Charlotte, N.C., GORE-TEX™ film, a microporous polytetrafluoroethylene film, available from W. L. Gore Associates, ZITEX™ film, a microporous polytetrafluoroethylene film, available from Norton Performance Plastics, Wayne, N.J., and DURAPORE™ film, a microporous hydrophilic film available from Millipore Products Division, Bedford, Mass. Other illustrative examples include microporous sheets of polyolefins, e.g., ethylene/propylene copolymers, polyvinylidene fluoride, polyester, and nylon. The sheet may consist essentially of one or more of the chosen polymeric films. The sheet may comprise special agents, e.g., hydrophilic or hydrophobic coatings as discussed below.

The support member acts as means for mounting the sample holder in a spectrometer. In a simple embodiment, as shown in FIG. 1, member 14 may be a strip or strips of pressure sensitive adhesive coated at one or more edges of one or both faces of sheet 12. The pressure sensitive adhesive enables holder 10 to be releasably mounted directly on the spectrometer (not shown) in the path of the beam (not shown). In some instances it will be desired that the adhesive be repositionable, non-outgassing, etc. Those skilled in the art will be able to readily identify and select many suitable adhesives for the desired application, e.g., heat-activated, particular tack characteristics, etc.

Figure 2:
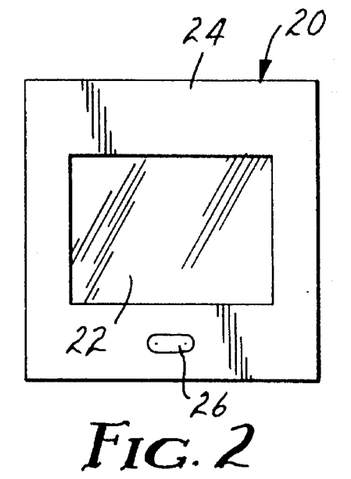
FIG. 2 is a plan view of one face of another illustrative embodiment of a sample holder of the invention.

FIG. 2 illustrates another embodiment of the invention wherein holder 20 has four edges and comprises sheet 22 and frame 24 as the support member. In this preferred embodiment, the means for mounting the sample holder comprises a frame, e.g., a photographic slide holder in which sheet 22 has been mounted as a photographic slide might have been. Frame 24 is preferably sufficiently stiff and sheet 22 mounted sufficiently tightly therein that sheet 22 is held flat across the transit opening when inserted into the spectroscopic device. As discussed above, sheet 22 is preferably very thin and thus may be subject to sagging or becoming creased or crinkled. It is important that the sheet be maintained substantially flat when the sample is in the spectroscopic device so that the IR beam passes through a constant amount of sample and to minimize the reflectance and scattering of the IR beam by the sheet which may cause interference in spectra obtained using the sample holder. The frame may be constructed of any suitable, relatively rigid material, e.g., plastic, paperboard, or metal.

In some instances it will be desirable for the prepared sample to be archived or stored for future reference. Accordingly, it is typically preferable that frame 24 be constructed of a material that may be written on or otherwise labeled so that pertinent information relating to the sample, e.g., sample or index number, may be noted thereon. Alternatively, label 26 or other additional information bearing media, e.g., microfilm, magnetic media, etc., may be included on frame 24 if desired. In some embodiments, the sample holder will further comprise a protective cover or flap (not shown) that, covers the transit opening during storage and is moved clear of the beam path during spectroscopic analysis.

The size and shape of frame 24 is dependent in part upon the sample cell receptacle of the particular spectroscopic instrument(s) in which holder 20 is to be used. Currently the industry typically uses sample holders that are about two inches wide. It has been found that standard photographic 35 millimeter slide mounts may be conveniently used as frames 24 for sample holders 20 of the invention. These slide mounts, which are typically made of plastic or paperboard, are readily available, can accommodate the microporous film and hold it flat, are sufficiently rigid, and fit easily into the sample holder mount of the instruments.

Sheet 22 may be secured in frame 24 by suitable means such as adhesive (e.g., pressure-sensitive or hot melt), sonic welding, or mechanical means. An advantage of some commercially available photographic slide mounts is that they possess adhesive, mechanical, or a combination of adhesive and mechanical mounting.

In the embodiment shown in FIG. 2, the sample may be placed on any portion of the transit opening of sheet 22, i.e., within the confines of frame 24, subject to the characteristics of the spectroscopic device being used.

Figure 3:
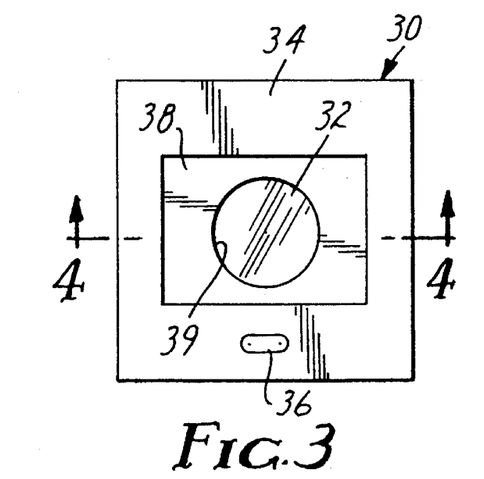
FIG. 3 is a plan view of one face of another illustrative embodiment of a sample holder of the invention comprising an aperture shield.
Figure 4:
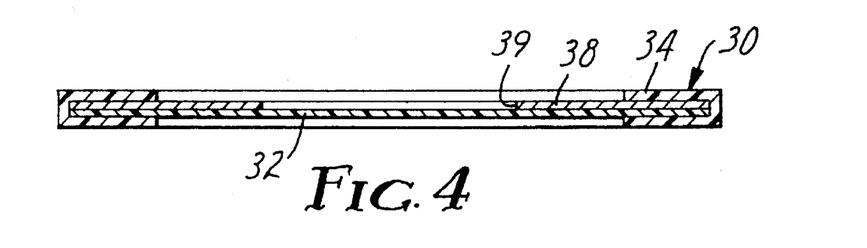
FIG. 4 is a cross-sectional view of the sample holder shown in FIG. 3 along axis 4—4.

In some instances it may be desired to restrict the area within the confines of the frame on which a sample is placed. FIG. 3 illustrates an embodiment wherein sample holder 30 comprises sheet 32 and frame 34. Holder 30 further comprises aperture shield 38 which covers a portion of sheet 32 and has transit opening 39 that leaves a portion of sheet 32 exposed on which the sample (not shown) would be placed. In use, the IR beam would pass through transit opening 39 and the sample located in opening 39. Aperture shield 38 is preferably substantially opaque to infrared light so that no interfering absorbances are produced and that incident light is not scattered. Preferably it has a transmittance in the range of about 4000 to about 400 $cm^{-1}$ of less than 10 percent and more preferably less than 1 percent. FIG. 4 illustrates holder 30 in cross-section along axis 4—4. The aperture shield may cover a portion of only one face of sheet 32 as shown on holder 30 in FIGS. 3 and 4, or it may cover portions of both faces of sheet 32, leaving at least one transit opening.

In some instances, aperture shield 38 may serve as a target to facilitate arrangement of the sample (not shown) on sheet 32 for spectroscopic analysis. In such instances, the shape, size, and location of transit opening 39 is dependent at least in part upon the characteristics of the spectroscopic device being used, particularly the geometric arrangement of the IR beam. In some instances, aperture shield 38 may serve as a small "work area" where samples can be applied to be transferred to the sheet for spectroscopic analysis. For instance, arrangement of samples of viscous materials such as plasticizers and adhesives is often facilitated by the availability of an aperture shield as a work area. Also, depending upon the configuration of frame 34 and characteristics of aperture shield 38, aperture shield 38 may impart greater stiffness of support to sheet 32.

The aperture shield may be made of the same material as the frame or other suitable material. In instances where a sample is to be processed in some fashion on the aperture shield prior to being placed on sheet 32 in transit opening 39, it is typically preferred that aperture shield not be wetted by the sample, so the sample is constrained to a small area and waste is minimized.

Aperture shield 38 may be secured with sheet 32 in frame 34 with suitable means, e.g., adhesive, sonic welding, or mechanical closures.

It will be understood that the shapes of the support member and the transit opening, and the aperture shield if used, may be of many different types, depending in part upon the construction of the holder, characteristics and specifications of the equipment with which the holder will be used, samples being analyzed, and preferences of individuals using the holder. For instance, the support member and aperture shield may be configured such that a sample holder has two or more transit openings.

Although neat (solventless) samples may be applied directly to the sample holder, it is more common to apply a sample that has been dissolved in solvent to facilitate handling. We have found that organic solvent based samples readily wet the surface of the microporous sheet with little or no swelling of the polymer matrix, and that the solvent quickly evaporates from the surface. It has also been unexpectedly found that latex solutions typically do not "skin over" as the solvent begins to evaporate, allowing a spectrum to be obtained. Samples which tend to skin over dry very slowly and trap unevaporated solvent(s) which can interfere with obtaining an accurate IR spectrum of the sample. While not wishing to be bound by theory, it is surmised that the microscopic pores in the sheet allow the surface of the polymer to be wetted by drawing the liquid in by capillary action. The solvent then readily evaporates due to the large surface area of the film. Typically, the solvent, if used, evaporates within 10 to 30 seconds from a sample of about 50 microliters. This may be accelerated by exposing the sample to an external heat source, such as a heat lamp, for a few seconds after application of the sample to the holder. Sample holders comprising sheets having pores that open through both surfaces, extending all the way through the sheet, can optimize this effect. After the solvent has been evaporated, the sample holder may be mounted in the spectrophotometer and a spectrum obtained.

An advantage of the sample holders of the invention is that they facilitate analysis of aqueous samples, biological fluids, etc. Although aqueous samples and samples of biological fluids may also be applied directly to the dry sample holder, it has been found advantageous to first apply a co-solvent to the sheet prior to applying the sample thereto. A co-solvent such as methanol pre-wets the sheet making it more receptive to the sample. The water and co-solvent may then be evaporated as previously described. For many water-based samples such as primers and adhesives, e.g., those that contain a surfactant, pre-wetting is often not necessary. With either of these procedures, spectra of water-based materials can be readily obtained without the use of expensive equipment such as ATR cells or resorting to other tedious sample preparation techniques.

Hydrophilic films have been found to be useful as sheets in spectroscopic analysis of aqueous samples. Such samples may be applied directly to the film without the need of pre-wetting as described above. In addition to aqueous samples, hydrophilic films would be useful in the analysis of biological fluids such as blood, sweat, tears, urine, semen, etc. Such samples may be applied directly to the sample holder without the need for lengthy sample preparation, and clear, distinct spectra may be obtained. Microporous sheets made of materials which are inherently hydrophilic or which are treated, e.g., by coating with suitable material or applying suitable treatment, to render them hydrophilic can be used herein.

In some embodiments, the polymer sheet may be treated to improve sample collection and retention properties. Depending upon the sheet material, treatment, and intended sample, the sheet may be treated prior to or during fabrication of the sample holder, or at later time prior to application or collection of the sample material.

For instance, the sheet may be exposed to corona treatment to impart an electrostatic charge thereto. Typically, when electrostatically-charged the sheet will have a substantially uniform charge across the transit opening with a side-to-side potential of at least about 100 volts/0.75 mil thickness. Electrostatic charges may be especially useful for collection and retention of greater quantities of fine particulate materials. By increasing retention of sample material on the holder, such sample holders also serve to reduce the amount of equipment cleaning and maintenance which may be required.

In another embodiment, at least a portion of the surface of the sheet is treated by application of a material, e.g., as a coating or graft polymerization, that will modify the interaction of the sheet with the desired sample material. For example, azlactone materials may be used to concentrate proteins in solution on a sample holder for infrared spectroscopic analysis.

Use of sample holders of the present invention allows for semi-quantitative, as well as qualitative, analysis of samples. Since the spectrum of any sample is a function of Beer's Law, the intensity of any peak (measured by peak height or area, total absorbance, or total transmittance) is a linear function of the amount of sample present. It is known that given the extinction coefficient for a particular peak or absorbance in a sample, the amount of sample present may be calculated. Alternatively, a series of samples may be prepared varying the loading, e.g., amount or concentration, of a sample. The intensities of a preselected absorbance may be plotted as a function of the loading, and the concentration of an unknown sample may then be determined by comparison with the plotted data. This is especially useful in the analysis of mixtures, where the concentration of a species in the mixture may be determined by the comparison of the relative peak heights of the constituents. For example, the relative amounts of saturated and unsaturated fats in edible oils may be easily determined by comparing C—H absorbances at 3010 $cm^1$ and 2854 $cm^{-1}$ as disclosed by Afran and Newbery in SPECTROSCOPY, 6(1), pp. 31–33, 1990, without resorting to ATR sample holders.

Sample holders of the present invention may also be used for tandem filtration/infrared analysis. Some of the microporous films used herein as sheets are known to be useful as filtration media. See for example Prasad, et al., Non-dispersive Solvent Extraction Using Microporous Membranes, New Membrane Materials and Processes for Separation, AIChE Symposium Series No. 261, vol. 84, 1988, pp. 42–53 and Baker et al., *Membrane Separation Systems—A Research and Development Needs Assessment*, Final Report, vol. 2, U.S. Dept. of Energy, Office of Program Analysis, Apr. 1990. In this technique two sample holders are positioned, each disposed horizontally, one over the other. A sample, containing an insoluble fraction, is then applied to the exposed sheet of the top sample holder. If desired, a spectrum of this starting material can be obtained. A portion of a suitable solvent is then applied to the sample, dissolving the soluble fraction(s) and washing it through the top sample holder onto the bottom sample holder. The insoluble fraction thus is filtered out of the sample by the top sample holder, on which it may subsequently be spectroscopically analyzed in accordance with the invention, and the soluble fraction is collected on the bottom sample holder, on which it may also be spectroscopically analyzed following evaporation of the solvent.

A variation of this technique also allows for the analysis of soluble materials from surfaces. By this technique, a sample holder may be placed on the surface of a solid object. Solvent is then applied so that the solvent is in contact with both the surface and the sample holder. The soluble materials from the surface will be extracted onto the surface of the sheet. The solvent may then be evaporated and the sample spectroscopically analyzed.

An advantage of the sample holders of the invention is that, while providing good analytical results, they may be sufficiently inexpensive to be discarded after use. Thus, the need to clean and polish the sample holders for reuse is avoided. Furthermore, the analyst may be spared further exposure to hazardous samples as well as exposure to potentially harmful solvents such as are used in cleaning and reconditioning conventional sample holders, e.g., chloroform, methylene chloride, and toluene. Also, if desired, the sample holder may be stored or archived for future reference. For instance, it is sometimes necessary to compare the spectra of materials with the spectra of known standard samples, and in some instances it is necessary to compare spectra during the course of a chemical reaction or process. It has been found that sample holders of the present invention may be stored with samples applied thereto, and analyzed at a later date with little or no degradation in the spectra of many samples. Due to the microporous structure of the sheet, the sample typically penetrates the pores in the sheet and is securely held on the sheet. Thus, there is typically little tendency to lose sample from the surface, and due to the chemical inertness of, for example, microporous polyethylene, there is little tendency of the sample to react with the sheet and thereby be altered or degraded. Accordingly, sample holders of the invention are well-suited for use in aging and degradation studies of materials.

The sample holders provided herein may be used with conventional "autosamplers", enabling large numbers of samples to be automatically analyzed and their spectra recorded. One such "autosampler" is Nicolet 912A0076, available from Nicolet Instruments, Madison, Wis. With such devices, a number of samples are loaded into a carousel, which automatically advances each sample holder into the infrared beam, obtains the spectrum, and then advances to the next sample. A common form of sample holder now used with such devices is a square plastic holder, approximately 5 by 5 centimeters, with a rectangular opening, approximately 2.2 by 3.5 centimeters, across which a rigid, self-supporting sample is secured. Such sample holders may be modified in accordance with the instant invention by providing a microporous sheet as described herein across the opening.

Samples holders of the invention may be used to provide a surprising and convenient method of performing spectroscopic analysis. In general, the method for spectroscopic analysis provided herein comprises:

a) providing a sample holder as described herein;

b) applying the sample to the sheet exposed in the transit opening of the sample holder;

c) transmitting infrared radiation through the sample and the sheet, i.e., projecting such radiation to one face of the sample holder and sample; and d) analyzing the radiation transmitted through the sample and sheet in a spectral region of interest.

If the sample contains solvent, it may optionally be allowed to dry after being applied to the sample holder prior to transmitting infrared radiation therethrough for the analysis. As discussed above, the baseline transmittance of the sample holder may be determined prior to applying the sample thereto. If desired and if the sample is a material that is soluble, it may be dissolved in a suitable: solvent, e.g., water, toluene, methylene chloride, methyl ethyl ketone, etc., prior to applying the sample to the sample holder. Solvents may be used to facilitate handling of sample materials and/or obtaining sample materials, e.g., by extraction. Samples which are in the form of fine particles and powders may be directly analyzed on sample holders of the invention without being solubilized if desired.

In a simple embodiment, a supply, e.g., roll of microporous sheet material may be fed into a spectroscopic analyzing device, secured in position and held flat by support members such as clips or brackets on the device, with a sample thereon. In this embodiment of the invention, the support member engages releasably with the sheet.

EXAMPLES

The invention will be further explained by the following illustrative, non-limiting examples which demonstrate the utility of several embodiments of sample holders of the invention and a variety of samples that can be analyzed in accordance with the invention. Comparisons with conventional sample holders are provided in some instances.

The evaluation of the quality of spectra obtained using sample holders of the invention is often empirical. For qualitative analysis it is often necessary to identify only the chemical species present in a sample, or the constituents in a mixture. The sample holder may be evaluated by comparing the spectra obtained with the standard spectra from a spectral library, available either in print or electronic form. There are many such spectral libraries available including the Sadtler Library of Electronic Spectra, the Aldrich/Nicolet FTIR Spectral Library, and the Aldrich/Nicolet Vapor Phase Spectral Library. The Nicolet/Hummel polymer spectral library, an electronic library available from Nicolet Instruments, Madison, Wis., contains the spectra of about 1800 compounds. Additional user generated libraries can be created by the analyst for performing spectral searching. In the evaluation of spectra obtained using the sample holder of the invention, the spectra were obtained and searched against the spectral library by either manual comparison of the spectra, or by searching the obtained spectra against the electronic library. The computer searches the library vs. the obtained spectra using various algorithms. The computer responds with either a compound or a list of compounds that are possible matches. Each such match has a corresponding "hit number" which is a measure of the confidence level of the match. Zero usually represents an absolute match, whereas a hit number in the range of 100 to 200 indicates a likely match, and so forth. The choice of confidence level is up to the discretion of the analyst.

The spectra were obtained using either a Nicolet 5-SXC FTIR, Analect model FX-6000 FTIR, or Digilab Model FTS 40. For the purposes of evaluating the sample holder, these instruments could be used interchangeably.

Examples 1–114

In all instances, the support member held the sheet substantially flat across the transit opening. Two types of sample holders were used. In a first type, the support member was a 5 centimeter by 7.5 centimeter (2 inch by 3 inch) cardboard rectangle in which a 1.6 centimeter (⅝ inch) diameter circular hole or transit opening was die-cut. A microporous sheet was secured to the card by means of double-sided adhesive tape. The sheet was lightly stretched as it was secured so it was held flat in the frame. In a second type, the sample holder comprised a commercially obtained photographic slide mount as a sample holder with a piece of polyester slide film having a two centimeter diameter circular hole therein as an aperture shield. The sheet was bonded to the aperture shield with double-sided adhesive tape. The slide mount crimped the aperture shield, mechanically securing them in place.

Table I has been organized broadly by sample type, e.g., adhesives, acids or acidic samples, polymeric additives, biological fluids, dyes, food products, fluorochemicals, etc. In some instances, comparative tests were run using conventional sample holders and analysis techniques. The Table indicates the conventional sample holder and sample application technique used (where applicable), the microporous sheet used in the sample holder of the invention and the sample application technique used in accordance with the invention, and comments on the spectra obtained.

The porosity and pore sizes of some of the sheets were evaluated by measuring the void volume (as determined in ASTM D-792), bubble point (as determined in ASTM F-316) and Gurley value (as determined in ASTM D726-84).

The following abbreviations are used in the Examples.

| Conventional Methods Sample Holder Types | |
|---|---|
| Abbrev. | Meaning |
| A | Silver bromide plate |
| F | Sample pressed out into self-supporting film |
| H | Horizontal ATR |
| K | Sample mulled with potassium bromide and formed into pellets |
| LC | Liquid Cell |
| NA | Not analyzed because very corrosive material |
| S | Sodium chloride plate |
| T | TEFLON ™, or other inert film |

| Application Techniques | |
|---|---|
| Abbrev. | Meaning |
| FIL | A film of sample material is made and transferred to sample holder |
| HTR | Sample is applied to a horizontal ATR-usually by pouring |
| KBR | Mulled with potassium bromide and formed into pellet |
| LIB | Internally generated library spectra |
| LIQ | Sample is placed between two salt plates, or a liquid cell |
| LIT | Published Infrared spectra |
| MEL | Solid sample melted directly onto plate and allowed to cool |
| NA | Not analyzed because very corrosive material |
| NEA | Sample was volatile liquid applied between two salt plates |
| PLA | Film formed from a solution of sample on plate |
| REF | A reference spectra obtained during analysis |
| SME | Viscous sample smeared onto sample holder |

| Invention Sheet Types | |
|---|---|
| Abbrev. | Meaning |
| A 85% percent void | 7.6 micron high density polyethylene, volume, 19 second/50 cc Gurley |
| B | 15.2 micron polyethylene, 80 to 85 percent void volume, 25 to 35 second/50 cc Gurley, 0.12 bubble point |
| C | 19.0 micron polyethylene, 16 second/50 cc Gurley, 71 percent void volume |
| D | CELGARD ™ K87B, 19.0 micron polyethylene, 75 second/50 cc Gurley |
| E | CELGARD ™ 2500, 25 micron polypropylene, 125 second/50 cc Gurley |
| F | ZITEX ™ A-110, 64 micron TEFLON ™, 30–60 micron pore size |

-continued

| | Invention Sheet Types |
|---|---|
| Abbrev. | Meaning |
| G | Polyethylene with hydrophilic coating 43 micron, 69.9 percent void volume, 18.7 second/50 cc Gurley, 0.48 bubble point |
| H | High density polyethylene with hydrophilic coating |
| I | Polyethylene with hydrophilic coating |
| J | Polyethylene with hydrophilic coating 7.6 micron, 85 percent void volume, 19.0 second/50 cc Gurley, 0.3 micron bubble point |

Sheets A, B, and C were prepared as disclosed in the aforementioned U.S. Pat. No. 4,539,256 which is incorporated herein by reference.

Sheets G and J were prepared as follows. Syndiotactic poly(vinyl trifluoroacetate), poly(vinyl alcohol) precursor, was prepared in a one gallon glass bowl jacketed pressure reactor having a stainless steel lid fitted with a metal turbine agitator blade on a sealed shaft, two mixing vanes, a thermowell, and at least two valved openings. The system was purged with a sweep of dried argon to remove moisture and oxygen before adding reactants or solvent. Materials were weighed and transferred in closed vessels under inert gas and anhydrous conditions. Charges were made through rubber septa covering the opened valves in the reactor lid using proper techniques to prevent uptake of atmospheric moisture and oxygen. Into the reactor were placed, in order, 3025 grams of FREON 113, 17.5 milliliters of a premix containing 2.5 grams of trifluoroacetic anhydride in 25 milliliters of FREON 113,355 grams vinyl trifluoroacetate monomer, 14 milliliters of a second premix containing 2.5 grams of bis(4-t-butylcyclohexyl) peroxydicarbonate (commercially available as PERCADOX 16 Normal from Akzo Chemie America, Noury Chemicals of Chicago, Ill.) in 25 milliliters of FREON 113. The reactor temperature was raised to 45° C. and maintained at that temperature for about 18 hours with an agitator speed of about 1000 rpm. A slight exotherm was observed during the reaction with a maximum system pressure of about 10 to 12 pounds/inch$^2$-gauge (0.7 to 0.8 kilogram/centimeter$^2$). The polymerized, syndiotactic poly(vinyl trifluoroacetate) (PVTFA) was isolated by filtration and dried at 40° under vacuum overnight.

A microporous polyethylene membrane, made by thermally induced phase separation as disclosed in Example 23 of the aforementioned U.S. Pat. No. 4,539,256, which is incorporated herein by reference, was saturation treated with a solution of about 4 weight percent of PVTFA in acetone using an extrusion die. The membrane was dried slowly for 1.6 minutes in a two zone air flotation oven with the two zones set at temperatures of 27° C. and 38° C. respectively to drive off the acetone resulting in a 22.2 weight percent add on of the PVTFA shell formed on the external and internal pore surfaces. No substantial blocking of the pores occurred, nor was an PVTFA skin formed on the covered side as evidenced from scanning electron microscopy (SEM) analysis. The complex geometric configuration of the membrane was substantially retained.

A piece of this dry membrane was placed in an ammonia-saturated glass vessel for 2 minutes in order to convert, in-situ, the PVTFA shell to a poly(vinyl alcohol) (PVA) shell. The ammonia atmosphere was generated by placing a concentrated ammonium hydroxide solution in the bottom of the vessel. A 68 weight percent reduction in the weight of the shell resulted from the hydrolysis reaction. This amount of weight loss corresponded exactly to the amount of weight loss expected for 100% conversion from PVTFA to PVA. Upon removing the membrane from the ammonia atmosphere, it displayed spontaneous and nearly instantaneous wetting with water. The complex geometric configuration of the membrane was substantially retained throughout the hydrolysis treatment as was evidenced by a pore size loss of less than 8 percent.

| | Application Techniques |
|---|---|
| Abbrev. | Meaning |
| DRO | Drops of the sample placed directly on sheet |
| PFE | Filtered sample from a second sample holder |
| PHEA | Sample heated in oven to induce heat-transfer to porous sheet |
| POW | Powder or small particle size solids applied directly to sheet surface |
| SME | Viscous sample smeared onto sheet |
| SPR | Sample dissolved in organic solvent and then sprayed onto porous film |
| SPW | Porous sheet was prewetted with organic solvent, then sample applied thereto |

| | Comments On Spectra |
|---|---|
| Abbrev. | Meaning |
| A | Sheet absorbances not totally subtracted from sample spectra |
| B | Relative peak height differences between conventional and invention methods |
| C | Greater than a 5 cm$^{-1}$ shift for at least one absorption peak |
| D | If bound water present by conventional methods, not observed by method of invention |
| E | Interference fringes observed using method of invention |
| F | Additional spectral information observed because of sheet's IR transmittance below 400 cm$^{-1}$ |
| G | Addition, or loss of, spectroscopic peaks occurred using method of invention compared to same regions with conventional methods |
| H | Residual solvents present by conventional methods, not observed with method of invention |
| I | Spectral information in the 2800 to 3000 cm$^{-1}$ region lost when using porous polyethylene films |
| J | Peak shape and/or baseline is different than conventional methods |
| K | High baseline noise in some regions (usually greater than 3200 cm$^{-1}$) |
| L | Sample only analyzed to see if possible with method of invention, spectral comparisons to conventional method not made |

|  |  | Conventional Method | | Invention Method | | Spectral Comments |
| --- | --- | --- | --- | --- | --- | --- |
| Ex. # | Sample Description | Holder Type | Application Technique | Sheet Type | Application Technique | Spectral Observations |
| ADHESIVES: | | | | | | |
| 1 | Acrylate adhesive | | -- | B | PHEA | A,L |
| 2 | ELMER'S ™ Glue Stick | | REF | B | SME, PFE | A,L |
| 3a | ELMER'S ™ Contact Cement | S | SME | C | SME | E,G,I,J |
| 3b | ELMER'S ™ Contact Cement | S | SME | D | SME | L |
| 3c | ELMER'S ™ Contact Cement | S | SME | E | SME | L |
| 3d | ELMER'S ™ Contact Cement | S | SME | F | SME | L |
| 4a | ELMER'S ™ Professional Carpenter's Wood Glue | | | A | SME | K,L |
| 4b | ELMER'S ™ Professional Carpenter's Wood Glue | | | B | SME | K,L |
| 4c | ELMER'S ™ Professional Carpenter's Wood Glue | | | C | SME | K,L |
| 4d | ELMER'S ™ Professional Carpenter's Wood Glue | | | G | SME | K,L |
| 4e | ELMER'S ™ Professional Carpenter's Wood Glue | | | H | SME | K,L |
| 4f | ELMER'S ™ Professional Carpenter's Wood Glue | | | I | SME | K,L |
| 4g | ELMER'S ™ Professional Carpenter's Wood Glue | | | J | SME | K,L |
| 5a | ELMER'S ™ White Glue-All | H, A | LIT | A | SME | G |
| 5b | ELMER'S ™ White Glue-All | H, A | LIT | B | SME | L |
| 6a | KRATON ™ - PICCOTEX ™ Solvent Based Adhesive | S | SME | A | SME | L |
| 6b | KRATON ™ - PICCOTEX ™ Solvent Based Adhesive | S | SME | B | SME | L |
| 6c | KRATON ™ - PICCOTEX ™ Solvent Based Adhesive | S | SME | C | SME | H,I,J |
| 7 | Natural Rubber - Polyterpene Adhesive | S | SME | A | SME | I |
| 8 | Natural Rubber based adhesive | S | SME | A | SME | A,G,I,K |
| 9 | Pierce - Stevens 7089 Adhesive | S | SME | A | SME | I |
| 10a | Ross SUPERGLUE ™ | S | SME | A | SME | L |
| 10b | Ross SUPERGLUE ™ | S | SME | D | SME | B,C,G,I,J |
| 10c | Ross SUPERGLUE ™ | S | SME | E | SME | L |
| 10d | Ross SUPERGLUE ™ | S | SME | F | SME | L |
| 11 | Water Based Acrylate Adhesive | | | A | SME | I,L |
| ACIDS: | | | | | | |
| 12a | Adipic acid | K | KBR, LIT | A | DRO | L |
| 12b | Adipic acid | K | LIB | B | DRO | A,B,G |
| 13 | LIME-AWAY ™ | NA | NA | A | SME | A,L |
| 14 | SCRUB-FREE ™ | NA | NA | A | SME | A,L |
| 15 | THE WORKS ™ | NA | NA | A | SME | A,L |
| ADDITIVES: | | | | | | |
| 16 | Alumina Trihydrate | K | KBR | A | POW | B,C,F,I,J |
| 17 | Aluminum Oxide | K | KBR | A | POW | B,C,D,E,F,G,I,J |
| 18 | Aluminum Silicate | K | KBR | A | POW | C,E,F,I |
| 19 | Barium Lead Stabilizer | K | KBR | A | POW | B,D,I |
| 20 | Calcium Carbonate | K | KBR | A | POW | C,D,I,J |
| 21 | Calcium Zinc Molybdate | K | KBR | A | POW | A,B,C,D,E,I |
| 22 | Hydrated Alumina | K | KBR | A | POW | A,B,C,E,F,I |
| 23 | Kaolin Clay | K | KBR | A | POW | B,C,D,F,G |
| 24 | Lead Antimony | K | KBR | A | POW | B,C,D,I |
| 25 | Magnesium Carbonate | K | KBR | A | POW | B,C,D,F,I |
| 26a | POLYCUP ™ 172 crosslinker | S | SME | A | SME | L |
| 26d | POLYCUP ™ 172 crosslinker | S | SME | D | SME | L |
| 26e | POLYCUP ™ 172 crosslinker | S | SME | E | SME | L |
| 27e | POLYCUP ™ 172 crosslinker | S | SME | F | SME | L |
| 28f | POLYCUP ™ 172 crosslinker | S | SME | G | SME | G,I,J |
| 28g | POLYCUP ™ 172 crosslinker | S | SME | H | SME | G,I,J |
| 28h | POLYCUP ™ 172 crosslinker | S | SME | I | SME | G,I,J |
| 28i | POLYCUP ™ 172 crosslinker | S | SKE | J | SME | G,I,J |
| 29 | Talc | K | KBR | A | POW | B,D,G,I |
| 30a | Zinc Oxide | K | KBR | A | POW | A,B,C,D,J |
| BIOLOGICAL FLUIDS: | | | | | | |
| 31 | Blood | H | LIT | G | SME | A,B,G,I |
| DYES, INKS AND COLORANTS: | | | | | | |
| 32 | Blue Cu phthalocyanine dye | | | B | SME | A,L |
| 33 | Cyan Leuco Dye | K | KBR | A | DRO | A,B,C,G,I,J |
| 34 | Organic Solvent based Yellow Ink | | | B | SME | A,L |
| 35 | RDC Blue copper phthalocyanine dye -Aq. Suspension | | | B | DRO | A,L |
| 36 | Red Organic Solvent Based UV Ink | S | SME | B | SME, PFE | A,G,I,K |
| 37 | Water Based Violet Ink | | | B | SME | A,L |
| 38 | Yellow Leuco Dye | K | KBR | A | DRO | A,B,C,G,J |
| FLUOROCHEMICALS: | | | | | | |
| 39 | vinylidine fluoride/hexafluoropropylene copoly. | K | PLA | B | SME | A,C,G,J |
| 40 | TFE/propylene copolymer | | LIB | B,G | DRO | L |
| 41 | Perfluoro polyepichlorohydrin | | LIB | B | SME | A,J,L |

-continued

| | | Conventional Method | | Invention Method | | Spectral Comments |
|---|---|---|---|---|---|---|
| Ex. # | Sample Description | Holder Type | Application Technique | Sheet Type | Application Technique | Spectral Observations |
| FOOD PRODUCTS AND ADDITIVES: | | | | | | |
| 42 | Baking Soda | K | KBR | A | POW | L |
| 43 | BRER RABBIT ™ Green Label Molasses | | LIT | B | SME | B,C,G,I,J |
| 44a | Butter | | | B | SME | L |
| 44b | Butter | | | F | SME | I |
| 45 | Corn Starch | K | KBR | A | POW | L |
| 46 | Honey | | LIT | B | SME | B,C,G,I,J |
| 47 | KARO ™ Light Corn Syrup | | LIT | B | SME | B,C,G,I,J |
| 48 | KARO ™ Pancake Syrup | | LIT | B | SME | B,C,G,I,J |
| 49a | Margarine | | | B | SME | L |
| 49b | Margarine | | | F | SME | I |
| 50a | Sugar Water | | LIT | B | DRO | L |
| 50b | Sugar Water | | LIT | G | DRO | A,B,C,G,I,J |
| HOUSEHOLD PRODUCTS: | | | | | | |
| 51 | Hilton Hotel Hair Shampoo | | | B | SME | I,L |
| 52a | JET-DRY ™ Dishwashing Rinse Agent | H | HTR | A | SME | L |
| 52b | JET-DRY ™ Dishwashing Rinse Agent | H | HTR | B | SME | L |
| 52c | JET-DRY ™ Dishwashing Rinse Agent | H | HTR | C | SME | C,F,H,I,J |
| 52d | JET-DRY ™ Dishwashing Rinse Agent | H | HTR | D | SME | L |
| 52e | JET-DRY ™ Dishwashing Rinse Agent | H | HTR | E | SME | L |
| 52f | JET-DRY ™ Dishwashing Rinse Agent | H | HTR | F | SME | L |
| 53 | MENNEN ™ Speed Stick Musk Deodorant | | LIT | B | SME | E,G,I |
| 54a | SCOPE ™ Mouthwash | H | HTR, LIT | B | DRO | C,D,F,H,I |
| 54b | SCOPE ™ Mouthwash | H | HTR, LIT | D | DRO | L |
| 54c | SCOPE ™ Mouthwash | H | HTR, LIT | E | DRO | L |
| 54d | SCOPE ™ Mouthwash | H | HTR, LIT | F | DRO | L |
| 54e | SCOPE ™ Mouthwash | H | HTR, LIT | G | DRO | L |
| 54f | SCOPE ™ Mouthwash | H | HTR, LIT | H | DRO | L |
| 54g | SCOPE ™ Mouthwash | H | HTR, LIT | I | DRO | L |
| 54h | SCOPE ™ Mouthwash | H | HTR, LIT | J | DRO | L |
| 55 | SURE ™ Solid Powder Antiperspirant | | | B | SME | A,L |
| 56 | ZEREX ™ Antifreeze | | | A | SPW, SME | L |
| LATEX SOLUTIONS/EMULSIONS: | | | | | | |
| 57 | Ammonia Preserved Natural Rubber Latex Sol'n | T, A | HTR, SME | B | SME | I |
| 58 | HYCAR ™ 1552 Butadiene-Acrylonitrile Rubber | T, A | HTR, SME | B | SME | G,I,J |
| 59 | Polysar PL-999 Styrene Butadiene Rubber | T, A | HTR, SME | B | SME | H,I,J |
| 60 | RHOPLEX ™ TR-653, Acrylic Resin Emulsion | T, A | SME | A | SME | I |
| MISCELLANEOUS: | | | | | | |
| 61 | beta-Napthol | S | PLA | A | DRO | A,B,F,H |
| 62 | Cyclohexylamine in Hydrocarbon Solvent | | | B | DRO | A,L |
| 63a | SANTOVAR A ™ - Oxidized | K | KBR | A | DRO | L |
| 63b | SANTOVAR A ™ - Oxidized | K | KBR | D | DRO | L |
| 63c | SANTOVAR A ™ - Oxidized | K | KBR | E | DRO | B,E,G,I,J |
| 63d | SANTOVAR A ™ - Oxidized | K | KBR | F | DRO | L |
| OILS AND LUBRICANTS: | | | | | | |
| 64 | CENEX ™ ROAW 1000 | S, H | HTR, SME | A | SME | L |
| 65 | CENEX ™ ROAW 150 | S, H | HTR, SME | A | SME | A |
| 66 | CENEX ™ ROAW 1500 | S, H | HTR, SME | A | SME | L |
| 67 | CENEX ™ ROAW 300 | S, H | HTR, SME | A | SME | L |
| 68 | CENEX ™ ROAW 5EP | S | SME | A | SME | L |
| 69 | CENEX ™ ROAW 750 | S, H | HTR, SME | A | SME | L |
| 70 | HYDROTEX ™ 80/140, lubricant | S | SME | A | SME | A |
| 71 | HYDROTEX ™ lubricant | S | SME | A | SME | A,B |
| 72 | IMS ™ Silicone Mist in Aerosol Can | | LIT | A | SPR | I |
| 73 | Mineral oil | S | SME | A | SME | E,J |
| 74 | MOBIL ™ 10W40 motor oil - new | S | SME | A | SME | A |
| 75 | MOBIL ™ 10W40 Motor oil - used | S | SME | A | SME | A,E,G,J |
| 76 | MOBIL ™ 523 | S, H | SME | A | SME | L |
| 77 | MOBIL ™ 5HC-634 | S | SME | A | SME | A |
| 78 | MOBIL ™ 5W30 motor oil - new | S | SME | A | SME | L |
| 79 | MOBIL ™ 5W30 motor oil - used | S | SME | A | SME | L |
| 80 | MOBIL ™ 600w | S, H | HTR, SME | A | SME | A,J |
| 81 | MOBIL ™ 629 | S | SME | A | SME | L |
| 82 | Sears CRAFTSMAN ™ cutting oil | S | SME | A | SME | L |
| 83 | TEXACO ™ 150 | S | SME | A | SME | A |
| 84 | TEXACO ™ 320 | S | SME | A | SME | L |
| 85 | TEXACO ™ 390 | S, H | HTR, SME | A | SME | L |
| 86 | TEXACO ™ EP2 | S | SME | A | SME | A,B,G,J |
| PRIMERS: | | | | | | |

-continued

| | | Conventional Method | | Invention Method | | Spectral Comments |
|---|---|---|---|---|---|---|
| Ex. # | Sample Description | Holder Type | Application Technique | Sheet Type | Application Technique | Spectral Observations |
| 87a | COLOR TILE ™ Floor and Wall Primer Plus | H | HTR | A | SME | L |
| 87b | COLOR TILE ™ Floor and Wall Primer Plus | H | HTR | B | SME | L |
| 87c | COLOR TILE ™ Floor and Wall Primer Plus | H | HTR | C | SME | A,F,H,I |
| 88a | HYCAR ™/Crude Rubber Water Dispersed Primer | H, A, T | HTR, SME | A | SME | L |
| 88b | HYCAR ™/Crude Rubber Water Dispersed Primer | H, A, T | HTR, SME | B | SME | L |
| 88c | HYCAR ™/Crude Rubber Water Dispersed Primer | H, A, T | HTR, SME | C | SME | A,B,C,F,G,H,I,J |
| 89a | Polyacrylamide/SBR/Casein Primer | A | SME | B | SME | L |
| 89b | Polyacrylamide/SBR/Casein Primer | A | SME | C | SME | L |
| 89c | Polyacrylamide/SBR/Casein Primer | A | SME | G | SME | I,J |
| 89d | Polyacrylamide/SBR/Casein Primer | A | SME | H | SME | I,J |
| 89e | Polyacrylamide/SBR/Casein Primer | A | SME | I | SME | I,J |
| 89f | Polyacrylamide/SBR/Casein Primer | A | SME | J | SME | I,J |
| 90a | SBR-HYCAR ™ Water Based Primer | T, A | PLA | B | SME | L |
| 90b | SBR-HYCAR ™ Water Based Primer | T, A | PLA | C | SME | B,E,I,K |
| PROCESS AIDS: | | | | | | |
| 91 | ACRYLOID K-175 ™, Acrylic Polymer | K, S | KBR, PLA | A | DRO | A,I |
| 92 | Antimony Trioxide | K | KBR | A | POW | C,D,F,I |
| 93 | Barium-Cadmium Laurate Stabilizer | K | KBR | A | POW | B,D,G,I,J |
| 94 | Diammonium Phosphate | K | KBR | A | POW | B,C,G,I,J |
| 95 | Dibasic Lead Phosphate Stabilizer | K | KBR | A | POW | B,D,F |
| 96 | Dibasic Lead Stearate | K | KBR | A | POW | B,D,G,I,J |
| 97 | Sodium Tartrate | K | KBR | A | POW | B,C,D,F,G,I,J |
| PLASTICIZERS: | | | | | | |
| 98 | Diethylphthalate | S | SME | A | SME | I |
| 99 | PLASTHALL ™ P-7092 Plasticizer | | SME | B | SME | A,L |
| 100 | UNIFLEX ™ 312 Plasticizer | S | SME | A | SME | I |
| RESINS AND PLASTICS: | | | | | | |
| 101 | FORAL AX ™ Resin 40% in KOH | | REF | B | DRO | A,L |
| 102 | FORAL ™ 65 Polyterpene resin | | HTR | B | DRO | A,L |
| 103 | Phenolic resin | | | B | SME, SPW | A,L |
| 104 | Polyvinyl Chloride Resin | S, F | PLA, FIL | A | SME | J |
| 105 | STA-TAC B ™ #47-450 Thermoplastic Resin | S | PLA, MEL | A | DRO | G,I |
| 106 | STAYBELITE ™ ester - 3 | | PLA | B | DRO | A,G |
| SOLVENTS: | | | | | | |
| 107 | C6 to C8 Hydrocarbon Blend | S, LC | NEA, LIQ | A | DRO | G,I |
| 108a | Methanol | | LIT | A | DRO | A,I |
| 108b | Methanol | | LIT | B | DRO | L |
| 108c | Methanol | | LIT | C | DRO | L |
| 109 | Toluene | LC, S | LIQ | A | DRO | F,I |
| SURFACTANTS: | | | | | | |
| 110a | IVORY ™ Dish Soap | H | HTR | B | SME | L |
| 110b | IVORY ™ Dish Soap | H | HTR | D | SME | L |
| 110c | IVORY ™ Dish Soap | H | HTR | E | SME | B,C,F,G,H |
| 110d | IVORY ™ Dish Soap | H | HTR | F | SME | L |
| 111 | TERGITOL ™ Surfactant | S | SME | B | SME | A,I,J |
| VARNISHERS: | | | | | | |
| 112 | CARVERS TRIPP ™ Water Based Varnish | | | A | SME | L |
| 113 | REZ ™ Solvent Based Varnish | S | SME | A | SME | I,J |
| 114 | SALLY HANSEN ™ Fingernail polish | S | SME | A | SME | A |

In some instances, spectra could not be obtained with conventional techniques due to the difficulty in handling some samples and limitations of the conventional techniques.

In all instances, analysis in accordance with the present invention provided fair to excellent spectra. Spectra were obtained with the method of the invention for aqueous-based, organic solvent soluble-based, and neat samples. Spectra were obtained with the method-of the invention for organic and inorganic samples, samples in the form of liquids and powders, viscous and non-viscous samples, polymeric samples, biological fluids, volatile and non-volatile samples, and of corrosive samples. The individual components of several complex mixtures could be identified in the spectra.

These examples illustrate the utility of the invention, demonstrating that spectra of a wide variety of samples may be obtained using microporous sheets as described herein, using a variety of sample collection and application techniques.

Examples 115 and 116

These Examples illustrate the use of electrostatically-charged microporous sheets in sample holders of the invention.

In each instance, the sheet was 15 micron thick microporous polyethylene with 74 percent void volume, 23 second/50 cubic centimeter Gurley, 0.9 bubble point, and residual oil content of 1.5 weight percent. When examined with a scanning electron microscope, the first side of the sheet was observed to have pores ranging in average characteristic width from 0.2 to 5 microns, with very few pores below about 1 micron in average characteristic width and the second side was observed to have pores ranging in average characteristic width from 0.2 to 2 microns, with very few pores below about 1 micron in average characteristic width.

Sheet material, in 7.5 by 20 centimeter (3 by 8 inch) pieces were corona treated on a flat plate corona treatment system at 16 kilovolts with 500 volt variation across the grid and about 0.2 milliamperes current, just sufficient to create a corona, to apply an electrostatic charge to the film. After treatment, the films were observed to have substantially uniform charges, positive and negative, respectively, of about 1400 volts on opposing sides. Initially, each side of the films was observed to have regions of positive charges and regions of negative charges with a maximum magnitude of about 100 volts.

The support members were like those used in the first type of sample holders used in Examples 1–114 except the support members were 5 by 10 centimeter (2 by 4 inch) rectangles in which a 1.9 centimeter (0.75 inch) diameter circular transit opening was die-cut.

Kaolin clay (DIXIE™ Clay from R. T. Vandervilt, a hydrated aluminum silicate, minimum 99.8 percent passes a U.S. Standard Sieve No. 325 fineness sieve, density is 2.59 to 2.65 grams/cubic centimeter, percent moisture is 1 percent maximum) was used as the sample material. Using a metal spatula, sample material was placed on the sheet exposed within the transit opening and the holder then turned on its side and lightly tapped to remove excess material. A very fine coating of sample material remained on the sheet.

It was observed that clay was retained better on the negatively charged sides of the sample holders than on the positively charged sides. Sample material was retained better on the negatively charged sides than on similar sample holders wherein the sheet had not been electrostatically charged. No side-to-side variation in sample retention was observed on the non-charged sample holders.

All sample holders in Examples 115 and 116 were prepared from the same lots of film, not charged and electrostatically charged, respectively, at the same time (with the exception of 116e which was prepared the next day). Each sample holder was loaded with kaolin clay and then spectroscopically analyzed in the powder sample compartment and then in the normal sample compartment of a Nicolet 710 Spectrometer as indicated. The next holder was then loaded with sample and analyzed spectroscopically with the following results reported in Table I ("L" refers to the location of the peak maximum and "H" refers to the peak height of the peak whose location is listed to the immediate left with baseline corrected). The test sequence was thus 115a in powder compartment then in normal compartment, 116a in powder compartment then in normal compartment, 115b in powder compartment then in normal compartment, 116b in powder compartment then in normal compartment, and so on.

TABLE I

| Example | Chge | Kaolin Clay | | | | | |
|---|---|---|---|---|---|---|---|
| | | L | H | L | H | L | H |
| Normal | | | | | | | |
| 115a | No | 3619.4 | 0.027 | 1036.4 | 0.110 | 545.9 | 0.060 |
| 115b | No | — | — | — | — | — | — |
| 115c | No | 3619.1 | 0.025 | 1036.7 | 0.099 | 546.9 | 0.051 |
| 115d | No | — | — | — | — | — | — |
| Powder | | | | | | | |
| 115a | No | 3619.1 | 0.022 | 1036.8 | 0.074 | 546.4 | 0.037 |
| 115b | No | 3618.9 | 0.009 | 1036.3 | 0.027 | 547.6 | 0.013 |
| 115c | No | 3618.9 | 0.022 | 1036.3 | 0.020 | 546.9 | 0.040 |
| 115d | No | — | — | — | — | — | — |
| Normal | | | | | | | |
| 116a | Yes | 3618.6 | 0.045 | 1035.9 | 0.216 | 545.0 | 0.117 |
| 116b | Yes | 3618.7 | 0.040 | 1036.0 | 0.168 | 545.3 | 0.090 |
| 116c | Yes | 3619.1 | 0.034 | 1036.5 | 0.130 | 547.4 | 0.068 |
| 116d | Yes | 3618.8 | 0.024 | 1036.3 | 0.100 | 547.2 | 0.053 |
| 116e | Yes | 3617.9 | 0.054 | 1034.6 | 0.325 | 543.2 | 0.174 |
| Powdered | | | | | | | |
| 116a | Yes | 3618.0 | 0.037 | 1035.8 | 0.209 | 544.5 | 0.115 |
| 116b | Yes | 3618.3 | 0.043 | 1035.9 | 0.192 | 545.0 | 0.103 |
| 116c | Yes | 3619.0 | 0.049 | 1036.4 | 0.168 | 547.8 | 0.085 |
| 116d | Yes | 3618.2 | 0.026 | 1035.9 | 0.112 | 546.5 | 0.063 |
| 116e | Yes | 3617.8 | 0.041 | 1034.8 | 0.270 | 540.7 | 0.141 |

The results for 115b and 115d in the normal compartment and 115d in the powder compartment were inadvertently not recorded.

Sample holders with charged sheets retain larger amounts of sample than do sample holders with non-charged sheets as evidenced by greater peak height. The charged sheets appear to loose this retentive power over time as evidenced by a decrease in peak height within the series from 116a to 116d. In 116a, sample material was applied to the holder 24 hours after the sheet had been cut from the charged roll and the holder assembled. In 116b, the respective time was 24 hours, 18 minutes, in 116c it was 46 hours, 18 minutes, and in 116d it was 46 hours, 31 minutes. When a new sample holder using a sheet freshly cut from the charged roll (116e) was prepared and tested about 8 hours after assembly of the holder, the elevated peak height was again observed. It is believed that the residual charge on the sheet in this sample holder was higher than that of the previously tested sample holders.

Examples 117–118

A new sample holder constructed like those used in Example 115 was used in Example 117 and the sample material was 5 micron silica.

A sample holder constructed like those used in Example 116 was used in Example 118 and the sample material was 5 micron silica.

It was observed that silica sample material was retained better on the negatively charged side than on the positively charged side. The following results were obtained with spectroscopic analysis:

TABLE II

| Example | Chge | Silica | | | | | |
|---|---|---|---|---|---|---|---|
| | | L | H | L | H | L | H |
| Powder | | | | | | | |
| 117 Normal | No | 1083.4 | 0.275 | 778.6 | 0.160 | 463.7 | 0.163 |
| 117 Powder | No | 1080.0 | 0.339 | 778.6 | 0.205 | 462.5 | 0.213 |
| 118 Normal | Yes | 1087.9 | 0.567 | 798.8 | 0.273 | 467.4 | 0.304 |
| 118 | Yes | 1085.9 | 0.517 | 798.7 | 0.247 | 466.2 | 0.285 |

Example 119

The sheet in this sample holder was polyethylene film having a thickness between about 175 and about 220 microns (6.9 and 8.7 mils) with concentric circular grooves of increasing radii on one side thereof. The grooves had a depth of between about 0 and about 190 microns (0 and 7.5 mils), being thicker in the middle and thinner at the outer edges of the pattern. The grooves were spaced between about 280 and about 485 microns (11 and 19 mils) apart, being closer in the center and more widely spaced at the edges.

TABLE III

| Example | Chge | Silica | | | | | |
|---|---|---|---|---|---|---|---|
| | | L | H | L | H | L | H |
| Powder | | | | | | | |
| 119 Normal | No | 1088.3 | 0.241 | 798.5 | 0.153 | 463.3 | 0.155 |
| 119 | No | 1090.4 | 0.520 | 799.0 | 0.272 | 465.0 | 0.306 |

Based on observed peak heights, sample holders with structured sheets appeared to retain as much silica as did sample holders with electrostatically charged sheets in prior examples.

Example 120

A microporous polyethylene film was produced as in Example 23 of U.S. Pat. No. 4,539,256 and rendered hydrophilic by coating with a solution of poly(vinyl trifluoroacetate) ("PVTFA") in acetone as described above. The resultant film was passed through an electron beam ("e-beam") chamber within a Model 1 Electrocurtain CB-300/30/380 (manufactured by Energy Sciences, Inc., Wilmington, Mass.) to generate free radicals. The accelerating voltage of the e-beam was 150 kilovolts with total irradiation dose of 50 kGys (5 Mrads). Film samples were passed through the e-beam equipment taped to a polyester carrier web traveling at 6.1 meters/minute.

The samples exited the e-beam chamber directly into a nitrogen ($N_2$) purged box where they were removed from the carrier and immersed into a 10 weight percent solution of 2-vinyl 4,4-dimethylazlactone in ethyl acetate for 3 to 5 minutes to undergo graft polymerization. The inert atmosphere was intended to prevent premature quenching of the generated radicals by oxygen ($O_2$). After immersion, the films were immersed in pure ethyl acetate to wash out excess monomer. They were then dried and placed in sealed plastic bags to prevent possible hydrolysis with atmospheric moisture. The film had increased weight by 7.4 percent.

Pieces of the sheet were secured across an aperture opening in a metal plate to yield a sample holder of the invention.

The initial film was spectroscopically analyzed and the ratio of the 1824 to the 1462 peak heights (ratio of azlactone carbonyl to polyethylene base sheet) was determined to be 0.415.

The first sample was vapors from a beaker containing a reagent grade aqueous solution of ammonium hydroxide. Sample material was applied by suspending a sample holder over the beaker for 1 minute. When spectroscopically analyzed the ratio of the 1824 to the 1462 peaks was determined to be 0.402. Reductions in this ratio indicate the carbonyl is reacting. The ratio of the vapor-exposed film showed a slight reduction from the original film.

The second sample was obtained by dipping the same piece of film into the ammonium hydroxide solution for 1 minute. After removal the film was dried with water/acetone rinses (which it is believed would not affect the ammonium sample) and again spectroscopically analyzed. The ratio was observed to have declined further to 0.334.

The same piece of film was then soaked in the solution for an additional three minutes and then dried as before. When spectroscopically analyzed, the ratio was observed to have declined substantially to 0.079.

This example shows that ammonium vapors and solution can be sampled and spectroscopically detected with a sample holder of the invention.

The last sample was allowed to sit at room temperature and allowed to sit for 4 days before being spectroscopically analyzed again. The resultant ratio was found to have declined only slightly to 0.076 indicating that the applied sample was being stably retained on the sample holder. This was a great improvement in stability compared to a previous sample of ammonium hydroxide solution applied to a sample holder with a hydrophilic sheet made of polyethylene and no azlactone. In that instance, the ammonia was retained for less than 30 seconds.

Example 121

A composite sample holder was made with a base sheet of (0.75 mil) thick microporous, 70 to 80 percent void volume, polyethylene having a basis weight about 0.5 grams/square centimeter and open mesh of blown microfiber made from polypropylene (Exxon 3505 G) having a basis weight of 8 grams/square meter. The open mesh contained numerous pores a millimeter or larger in average characteristic width.

Kaolin clay was the sample material applied as described in the prior examples. The sample material easily became entrained in the pores.

Spectroscopic analysis revealed peaks having substantially higher heights than obtained with sample holders having non-charged, charged, or structured sheets as shown below:

TABLE IV

| Example | Chge | L | H | L | H | L | H |
|---|---|---|---|---|---|---|---|
| Powder | | | | | | | |
| 121 Normal | No | 3622.0 | 0.310 | 1036.0 | 0.810 | 537.9 | 0.54 |
| 121 | No | 3619.6 | 0.490 | 1035.6 | 1.22 | 547.5 | 0.57 |

Various modifications and alterations of this invention will become apparent to those skilled in the art without departing from the scope and spirit of this invention.

What is claimed is:

1. A method for spectroscopically analyzing a sample, said method consisting essentially of:
   a) providing a sample holder consisting essentially of a microporous polymeric sheet, at least a portion of said sheet being an exposed transit area for placement of a sample thereon, said sheet being substantially flat across said transit area and having an average baseline transmittance of at least 1 percent and having a plurality of interconnecting microscopic pores opening through at least one face of said sheet, said pores ranging from about 0.1 to about 50 microns in width in their average characteristic width;
   b) applying said sample to said transit area of said sheet;
   c) transmitting infrared radiation through said sample and said sheet; and
   d) analyzing the radiation transmitted through said sample and said sheet in a spectral region of interest.

2. The method of claim 1 wherein said sample holder further comprises a support member.

3. The method of claim 1 further comprising determining the baseline transmittance of said sample holder prior to applying said sample thereto.

4. The method of claim 1 wherein said sample is a solvent soluble material and further comprising dissolving said sample in solvent prior to applying to said sample holder.

5. The method of claim 1 wherein said sample is applied to said sample holder by filtering a stream containing said sample with said sample holder.

6. The method of claim 1 wherein said sample is in the form of fine particles or powder when applied to said sample holder.

7. The method of claim 1 wherein said sample is a biological fluid.

8. The method of claim 1 wherein:
   a) two of said sample holders are positioned, one over another, each disposed horizontally;
   b) applying said sample to the top sample holder;
   c) applying a suitable solvent to said sample such that said solvent passes through said sample and said top sample holder onto said bottom sample holder; and then
   d) spectroscopically analyzing at least one of (1) the sample fraction on said top sample holder or (2) the sample fraction on said bottom sample holder carried there by said solvent.

9. The method of claim 1 wherein said sheet has an electrostatic charge on opposing sides.

10. The method of claim 1 wherein said sheet further comprises azlactone material.

11. The method of claim 10 wherein said sheet comprises a polymer material to which azlactone has been grafted.

12. The method of claim 1 wherein said sheet comprises a non-woven material.

13. The method of claim 1 wherein said sheet has at least one structured surface.

14. The method of claim 1 wherein said sheet comprises a composite comprising a base sheet and an open mesh.

15. The method of claim 1 wherein said sample is allowed to dry prior to said transmitting infrared radiation.

16. The method of claim 7 further comprising spectroscopically analyzing said sample after said applying said sample to said top sample holder and before said applying a suitable solvent to said sample.

17. The method of claim 1 wherein said sample is a material that readily crystallizes when put on a flat surface and wherein when said sample material is applied to said sheet crystallization is retarded.

18. A method for spectroscopically analyzing a sample, said method consisting essentially of:
   a) providing a sample holder consisting essentially of a microporous polymeric sheet, at least a portion of said sheet being an exposed transit area for placement of a sample thereon, said sheet having an average baseline transmittance of at least 1 percent and having a plurality of interconnecting microscopic pores opening through at least one face of said sheet, said pores ranging from about 0.1 to about 50 microns in width in their average characteristic width said sheet having pores opening through only one face thereof;
   b) applying said sample to said transit area of said sheet, said sample being applied to said face through which said pores open;
   c) transmitting infrared radiation through said sample and said sheet; and
   d) analyzing the radiation transmitted through said sample and said sheet in a spectral region of interest.

* * * * *

UNITED STATES PATENT AND TRADEMARK OFFICE
CERTIFICATE OF CORRECTION

PATENT NO.: 5,470,757
DATED: November 28, 1995
INVENTOR(S): James E. Gagnon et al.

It is certified that error appears in the above-identified patent and that said Letters Patent is hereby corrected as shown below:

In Column 12, Line 50, delete the colon immediately following the word "suitable".

In Column 16, Line 14, insert the following after the word "percent":
  (new paragraph) --Sheets D, E, and F were obtained commercially.--

In Column 21, Line 61, delete the comma immediately preceding the first word "obtained".

In Column 21, Line 63, delete the hyphen between the words "method" and "of".

Signed and Sealed this

Seventeenth Day of March, 1998

*Attest:*

BRUCE LEHMAN

*Attesting Officer*  Commissioner of Patents and Trademarks